US006475785B1

(12) United States Patent
Shi et al.

(10) Patent No.: US 6,475,785 B1
(45) Date of Patent: Nov. 5, 2002

(54) SINGLE-CHAIN POLYPEPTIDES COMPRISING TROPONIN I N-TERMINAL FRAGMENTS AND TROPONIN C

(75) Inventors: Qinwei Shi, Etobicoke; Shigui Liu, Mississauga; Mingfu Ling, Etobicoke, all of (CA)

(73) Assignee: Spectral Diagnostics, Inc., Toronto (CA)

( * ) Notice: Subject to any disclaimer, the term of this patent is extended or adjusted under 35 U.S.C. 154(b) by 0 days.

(21) Appl. No.: 09/368,819

(22) Filed: Aug. 5, 1999

Related U.S. Application Data

(63) Continuation-in-part of application No. 09/176,546, filed on Oct. 21, 1998, and a continuation-in-part of application No. 08/993,380, filed on Dec. 18, 1997, now Pat. No. 6,077,676.

(51) Int. Cl.[7] .......................... C12Q 1/00; G01N 33/53; C12P 1/00; C12P 21/06; A61K 38/00
(52) U.S. Cl. ........................... 435/325; 435/4; 435/7.1; 435/41; 435/69.1; 530/300; 530/350; 530/402
(58) Field of Search .................. 530/350, 402, 530/300; 435/4, 41, 69.1, 325, 7.1

(56) References Cited

U.S. PATENT DOCUMENTS

| 4,946,778 | A |   | 8/1990  | Ladner et al. |
| 5,290,678 | A |   | 3/1994  | Jackowski |
| 5,516,637 | A |   | 5/1996  | Huang et al. |
| 5,583,200 | A |   | 12/1996 | Larue et al. |
| 5,604,105 | A |   | 2/1997  | Jackowski |
| 6,077,676 | A | * | 6/2000  | Shi et al. |
| 6,248,869 | B1|   | 6/2001  | Morjana et al. |
| 6,268,481 | B1|   | 7/2001  | Morjana |

FOREIGN PATENT DOCUMENTS

| WO | WO 98/54218 | 12/1998 |
| WO | WO 98/54219 | 12/1998 |
| WO | WO 99/31235 |  6/1999 |

OTHER PUBLICATIONS

Promega Corporation, Promega Protocols Applications Guide, Second edition, pp. 277–279, 1991.*
Gasmi–Seabrook, G. et al. Solution Structures of the C–Terminal Domain of Cardiac Troponin C Free and Bound to the N–Terminal Domain of Cardiac Troponin I, Biochemistry 38:8313–8322, 1999.*
Lin et al. Covalent Binding of Peptides to the N–terminal Hydrophobic Region of Cardiac Troponin C Has Limited Effects on Function, Journal of Biological Chemistry 271(1):244–249, 1996.*
Dong et al. Conformation of the N–Terminal Segment of a Monocysteine Mutant of Troponin I from Cardiac Muscle, Biochemistry 36:6745–6753, 1997.*
Fujita–Backer et al., 1993, J Biochem, 114:438–44.
Hu et al., 1996, Protein Expression and Purification, 7:289–93.
Lindbladh et al., 1994, Biochem, 33:11692–8.
Malnic et al., 1994, Eur J Biochem, 222:49–54.
Vallins et al, 1990, FEBS Letters, 270:57–61.
Zhang et al., 1999, Recombinant single chain cardiac troponin I–C polypeptide: an ideal stable control material for cardiac troponin I immunoassays. Clinical Chemistry 45 (suppl. 6):A53.

* cited by examiner

*Primary Examiner*—Anthony C. Caputa
*Assistant Examiner*—Alana M. Harris
(74) *Attorney, Agent, or Firm*—Klauber & Jackson

(57) ABSTRACT

This invention relates to single-chain polypeptides and their genetic sequences comprising a human cardiac troponin I N-terminal fragment and troponin C. The N-terminal fragment may or may not have the intact N-terminus. The single-chain polypeptide may be expressed recombinantly, and a linker or spacer polypeptide or peptide may be interposed between the troponin sequences. The single-chain polypeptides have utility as controls or calibrators for troponin assays, for the purification of troponin subunits and as an antigen for the preparation of antibodies.

6 Claims, No Drawings

SINGLE-CHAIN POLYPEPTIDES COMPRISING TROPONIN I N-TERMINAL FRAGMENTS AND TROPONIN C

CROSS-REFERENCE TO RELATED APPLICATIONS

This application is a continuation-in-part of Ser. No, 09/176,546, filed Oct. 21, 1998, and a continuation-in-part of Ser. No. 08/993,380, filed Dec. 18, 1997, now U.S. Pat. No. 6,077,676. Benefit of priority to these applications is claimed under 35 U.S.C. § 120.

FIELD OF THE INVENTION

This invention relates to recombinantly-expressed, single-chain polypeptides comprising an N-terminal fragment of troponin I linked to troponin C, and their corresponding genetic sequences.

BACKGROUND OF THE INVENTION

Early and accurate assessment of suspected acute myocardial infarction is critically dependent on the sensitive and specific detection and quantitation in blood, serum or plasma of released cardiac muscle intracellular components in order to distinguish a potentially lethal event in need of emergency measures from non-life threatening conditions such as angina and non-cardiac chest pain such as dyspepsia. Early electrocardiographic changes are neither adequately specific nor sensitive, and the medical profession has come to rely on serum biochemical markers of cardiac tissue injury for early diagnosis. Initially, the serum markers creatine kinase (CK) and specifically the cardiac CK-MB isoform were used, and subsequently myoglobin as a more sensitive early indicator of cardiac damage. More recently, cardiac troponin complex and its subunits have come to be preferred as markers of myocardial damage because of their high specificity. These tests in combination, along with other markers of skeletal muscle damage, provide a high degree of diagnostic accuracy. If performed in the emergency room, an early and accurate diagnosis of myocardial damage offers great advantage to a suspected heart attack victim.

Diagnostic tests employing cardiac markers are described, for example, in U.S. Pat. Nos. 5 5,604,105 and 5,290,678. These and other procedures offer the rapidity of diagnosing myocardial infarction in the emergency room setting and offer significant medical benefit for patients. Diagnostic tests in which the level of troponin subunits or complexes is measured in bodily fluids frequently utilize purified troponin subunits or complexes as antigens for the preparation of antibodies used in the assay procedure, as well as the purified subunits or complex used as controls and calibrators in performing the assays. Assay calibrators are used to prepare a series of dilutions by which a standard curve across the operating range of an assay is prepared; assay controls are used to confirm that an assay is operating properly by ensuring that the assayed value of predetermined samples fall within an acceptable range established for each assay. In order for the assay to be calibrated properly, the troponin controls and calibrators must remain stable and in a form which is immunodetectable by the antibody.

Troponin is a muscle protein integrally involved in the calcium-dependent regulation of muscle contraction. Troponin exists in both cardiac and skeletal muscle as a non-covalently-bound complex of three subunits, the isoforms troponin C, the calcium-binding subunit, troponin I, the inhibitory subunit, and troponin T, which locates the troponin complex on tropomyosin. In vitro under the proper conditions, the troponin subunits will spontaneously associate to form non-covalently-bound complexes, e.g., troponin I and C, and troponin I, C, and T. Differences exist between the amino acid sequences of the cardiac muscle and skeletal muscle troponin isoforms.

Upon cardiac muscle injury and necrosis, troponin leaks from heart tissue into circulation, where its sensitive detection can help diagnose a heart attack. The amino acid sequence differences between the cardiac and skeletal muscle isoforms of the troponin subunits are exploited in diagnostic tests which specifically measure the cardiac isoform of the troponin subunits and complexes. Diagnostic tests for cardiac troponin I are available.

Numerous troponin preparations from both natural and recombinant sources have been described that contain troponin I together with troponin C. Malnic and Reinach (1994, Eur. J. Biochem., v. 222, pp. 49–54) produced a recombinant complex in vivo by cloning all three chicken skeletal muscle troponin subunits into one or more expression plasmids. Within the expression vector each troponin gene had its own promoter, and the proteins were expressed within the bacterium as individual troponin subunits, which subsequently formed complexes within the bacterium. Fujita-Becker et al. (1993, J. Biochem., v. 114, pp.438–444) described the reconstitution of rabbit skeletal troponin complex from recombinant subunits expressed in *E. coli*. None of these recombinant products has been demonstrated to have adequate stability for use as a diagnostic test standard or calibrator. As mentioned above, even the complexes of troponin subunits are not stable and will not remain intact and bound together in solution to any great extent.

As described in co-pending application Ser. No. 09/176,546, filed Oct. 21, 1998, incorporated herein by reference, troponin I is inherently of poor structural stability, and is subject to proteolytic cleavage by proteases present in biological samples. A troponin I material prepared in a bodily fluid matrix is thus subject to conformational alteration and degradation and is unsuitable as a calibrator or control. Furthermore, the inherently more stable troponin complexes are known to dissociate on storage and dilution, and thus become susceptible to proteolytic degradation. In the instance of troponin I, it must be complexed with troponin C in order to help maintain its conformational structure and stability; however, because of the nature of the affinity of the subunits in the complex, the fraction of the troponin I present in the form of a complex is concentration dependent. This limits its utility as an assay calibrator or control. The extent of interactions between the subunits may be calculated from the dissociation constant, $K_d$ [for example, as reported in Biochemistry 33:12729 [1994]]. By calculation and experimental measurement, only a limited amount of troponin I is bound to troponin C over the range that would be found in patient serum samples, and thus the levels at which calibrators and controls must be used. For example, at 50 ng/ml, the upper range of most troponin I assays, only 10% of the troponin I is bound to troponin C when the two subunits are present at a ratio of 1:1. With up to 10-fold more troponin C to troponin I, and in the presence of divalent cations, a claim (Larue et al., U.S. Pat. No. 5,583,200) to the stability of the complex in the cold was minimal, i.e., "at least one day." Maintaining higher concentrations of the complex decreases the degree of dissociation; however, after dilution to the level necessary to calibrate an assay, the subunits dissociate and become immunologically unstable. Dissociation then subjects the subunits to proteolytic attack, further reducing the utility of such calibrators and controls. As described in the above-identified application, stable N-terminal fragments of troponin I, optionally with an intact N-terminus, are described which are immunostable and are useful as calibrators and controls for optimized troponin I assays. Furthermore, as described in U.S. Pat. No. 6,077,676, incorporated herein by reference, a stable troponin preparation for assay and other uses has been described which comprises troponin I and troponin C on a single polypeptide chain, prepared as a recombinant construct and expressed in a bacterial expression system as a single polypeptide. As noted above, association of troponin I and troponin C protects the troponin I molecule from conformational changes and proteolytic attack; in the single-chain construct, the troponin subunits cannot dissociate, and thus the troponin I is immunostable and resistant to proteolytic degradation.

It is towards the development of an immunostable and immunodetectable troponin I composition that the present invention is directed.

The citation of any reference herein should not be construed as an admission that such reference is available as "Prior Art" to the instant application.

GLOSSARY

"N-terminal fragment of troponin F" refers to a portion of the troponin I molecule derived from the N-terminal part of the native molecule, which may be any fragment from the N-terminus (amino acid 1) to about the middle of the native molecule (about amino acid 110). The N-terminal fragment may or may not have the native N-terminus. A non-limiting example is an 82 amino acid fragment corresponding to amino acids 28 through 110 of native human cardiac troponin I.

"N-terminus" is the N-terminal amino acid 1 of native troponin I.

"Linker" refers to a sequence of about 5 to about 50 amino acids (and its corresponding polynucleotide sequence) interposed between the troponin I fragment and troponin C of the present invention to permit the troponin molecules to associate in a fashion similar to their association in the native non-covalent troponin I-troponin C complex.

"Spacer" refers to a short amino acid sequence of about 4 or fewer amino acids (and its corresponding polynucleotide sequence) interposed between the troponin I fragment and troponin C for the purpose of facilitating the preparation of the recombinant construct using a short restriction site.

SUMMARY OF THE INVENTION

It is a principal objective of the present invention to provide single-chain polypeptides comprising an N-terminal fragment of troponin I and troponin C. The presence of the troponin I N-terminal fragment and troponin C on the same polypeptide chain confers conformational stability and immunostability to the product. Portions of the single-chain polypeptide comprising an N-terminal fragment of troponin I, optionally lacking the N-terminus, resemble the stable circulating form of troponin I which is partially degraded by proteinases, either at the amino end, the carboxy end or both are similar to the main serum form that is measured in a patient's blood sample for identifying the cause of chest pain and, more specifically, to diagnose a heart attack. The circulating, partially degraded form of troponin I joined to troponin C on the same polypeptide provide stable compositions substantially similar in structure to the analyte being measured and with epitopes which will combine with the analyte. They provide immunostable and immunodetectable compositions suitable for use as calibrators and controls for troponin I immunoassays, as well as for affinity purification of troponin antibodies.

The single-chain polypeptide may preferably include a linker sequence interposed between the sequences of the N-terminal troponin I fragment and troponin C. The sequence of the linker peptide is chosen so that it does not interfere with the tertiary structure of the product and therefore its aforementioned useful properties. A single-chain polypeptide in which an N-terminal fragment of troponin I and troponin C are joined, optionally through a linker peptide, provides a stable, reproducible, and easily purified material for the development of troponin assays, an antigen for preparing troponin antibodies, as well as material for use as controls and calibrators for troponin assays. A non-limiting example of an N-terminal fragment of troponin I joined through a linker sequence to troponin C is that of SEQ ID NO:2. In this example, the troponin I fragment comprises residues 28 through 110 of native troponin I, joined through a 19-amino acid linker sequence to native troponin C. In a further example, SEQ ID NO:4 represents a single-chain polypeptide comprising an N-terminal fragment of troponin I, residues 28 to 110 of native troponin I, linked to the native troponfin C sequence without a linker. In order to engineer the construct, a two amino acid sequence is provided between the troponin portions.

The N-terminal fragment of troponin I is optionally lacking the N-terminus. The fragments of human cardiac troponin I in the compositions of the present invention comprises the intact N-terminus of troponin I and that portion extending to about amino acid residues 95 to about 105 of native troponin I. In an another embodiment, about 20 to about 30 amino acids of the N-terminal portion may be absent. Thus, the N-terminal troponin I fragment of the single-chain polypeptide of the present invention provides an N-terminal troponin I fragment of about 65 to about 85 amino acids. By way of non-limiting examples, the single-chain polypeptides SEQ ID NO:2 and SEQ ID NO:4 have amino acids 28 through 110 of native troponin I.

The single-chain polypeptide of the present invention is prepared most readily by recombinant techniques, by constructing a replicable cloning or expression vehicle such as a plasmid carrying the genetic sequence for the single-chain polypeptide, and transforming a host cell, such as *E. coli*, with the vehicle such as a plasmid, and expressing the polypeptide by the host cell. The single-chain construct may contain a linker peptide sequence between the troponin I fragment and the troponin C amino acid sequences, such sequence introduced by recombinant means. If no linker peptide is provided, an optional short sequence of about two amino acids may be provided between the troponin sequences in order to engineer the construct. Certain modifications may be made in the genetic sequence of the polynucleotide, with or without changes in the consequent amino acid sequence of the polypeptide, in order to improve the expression of the polypeptide in the host cell. These changes do not alter the properties of utilities of the single-chain polypeptide for the aforementioned purposes.

It is a further aspect of the invention to provide methods for using the single-chain polypeptides described hereinabove as calibrators or controls for troponin I assays.

It is another object of the present invention to provide a genetic sequence for a single-chain polypeptide comprising a genetic sequence of an N-terminal fragment of troponin I, optionally lacking the N-terminus, and troponin C. The genetic sequence may also include a linker genetic sequence interposed between the genetic sequences of troponin I and troponin C. In the absence of a linker sequence, a short sequence equivalent to two amino acids may be introduced therebetween to enable the engineering of the construct. A host cell may be transformed with the replicatable cloning or expression vehicle containing the aforementioned genetic sequences. As mentioned above, certain changes to the genetic sequence of the troponins may be made in order to facilitate expression in the host cell.

It is a further object of the present invention to provide a host cell containing a cloning or expression vehicle such as a plasmid carrying the genetic sequence for a single-chain polypeptide chain comprising the genetic sequences of an N-terminal troponin I fragment and troponin C, and capable of expressing a single-chain polypeptide comprising troponin I and troponin C.

These and other aspects of the present invention will be better appreciated by reference to the following Detailed Description.

DETAILED DESCRIPTION OF THE INVENTION

For utility as stable calibrators and controls for troponin I assays, the compositions of the present invention improve upon the inherent conformational instability and proteolytic susceptibility of free troponin I, the instability of association of the troponin I-troponin C complex, and the dissimilarity between the predominant circulating form of troponin I in a sample and the native troponin I analytes. The improvements consists of a single-chain polypeptide comprising an N-terminal fragment of human cardiac troponin I and cardiac troponin C. The troponin subunits are covalently linked through a peptide bond and reside on the same linear polypeptide, providing a stable troponin I fragment-troponin C single-chain polypeptide to meet the needs of the industry. The N-terminal fragment of troponin I in the polypeptide resembles the main form of troponin I in circulation, following partial degradation by intracellular proteinases and serum proteinases, which cleave the C-terminal portion of troponin I, leaving an intact N-terminal fragment, which may be further cleaved at the N-terminal portion. The remaining fragment of troponin I, approximately between amino acids 28 and 110, is highly resistant to further proteolytic degradation due to its primary structure. Stability of the tertiary structure of the troponin I fragment is conferred by association with troponin C. Thus, a single chain troponin I N-terminal fragment and troponin C construct provides a degradation resistant and structurally stable polypeptide, which is in a form similar to that of the main serum analyte.

The single-chain polypeptide may be prepared by recombinant techniques, and may optionally include a linker polypeptide or a spacer polypeptide sequence interposed between the troponin I and troponin C sequences.

For example, one embodiment of the troponin I fragment-troponin C single-chain polypeptide may comprise a troponin I fragment at the N-terminal portion of the polypeptide, with the C-terminus of the troponin I fragment sequence engaged in a peptide bond with the N-terminus of the troponin C sequence. In one non-limiting example, in order to engineer such a construct, a short sequence of amino acids, about 2 is provided between the troponin molecules. This permits the use of restriction endonucleases in preparing the construct. For example, the SphI endonuclease site codes for Ala Cys. In another embodiment, a construct in which the troponin I fragment is joined directly to the troponin C may be prepared by techniques such as solid-phase synthesis, of either the polynucleotide or the protein, or use of the SOEing procedure described below. In a second embodiment wherein a linker peptide sequence is interposed between the troponin I fragment and the troponin C amino acid sequences, one preferable arrangement comprises the troponin I fragment sequence at the N-terminal portion of the polypeptide, its C-terminus engaged in a peptide bond with the N-terminus of the linker peptide, and the C-terminus of the linker peptide then engaged in a peptide bond with the N-terminus of the troponin C sequence. An example of this construct is the amino acid sequence depicted in SEQ ID NO:2. In this example, the amino acid sequence of the linker is represented in SEQ ID NO:6. It contains 19 amino acids. The polynucleotide sequence of the linker is depicted in SEQ ID NO:5. It should be noted that in engineering the construct with the linker, nucleotides equivalent to an additional two amino acids is introduced at each end of the linker polynucleotide in preparing the construct. As referred to herein, the linker sequence comprises the linker sequence and the two amino acids at each end to facilitate the engineering of the product. As mentioned above, the intermediate amino acids may be omitted if alternate methods of preparing the product are used, for example, by solid phase synthesis of the polynucleotide or the amino acid sequence, by use of the SOEing method (see below), or by identifying restriction endonucleases which exactly recognize the termini of the troponin species and linker sequences being linked.

The amino acid sequences in the above example correspond to the nucleotide sequences of the cDNA coding for these polypeptides. The genetic sequence in the first example comprises the troponin I fragment genetic sequence at the 5' end of the cDNA, its 3' end followed immediately by two intermediate codons and then the 5' end of the troponin C genetic sequence. An example of the polynucleotide construct is SEQ ID NO:3. In the preferred embodiment wherein a linker is interposed between the troponin I and troponin C sequences, the 5' of the cDNA sequence begins with the troponin I genetic sequence, its 3' end followed by the 5' end of the optional interposed linker genetic sequence, and its 3' end followed by the 5' end of the troponin C genetic sequence, ending at the 3' end of the cDNA. In the specific example above, the genetic sequence is represented in SEQ ID NO: 1. The cDNA sequence of the linker is presented in SEQ ID NO:5.

As described above, selection of the length and specific sequence of the optional linker polypeptide is limited only in that it must not interfere with the immunodetectability of the troponin I fragment on the single-chain polypeptide. It is believed that with a suitable linker sequence, the troponin I fragment and the troponin C of the single polypeptide chain associate with each other in a similar fashion as they do in a non-covalent troponin I-troponin C complex, and the attachment of the subunits in the single polypeptide chain maintains the conformation of the association and thus the consistent immunodetectability of the troponin. Furthermore, a troponin I fragment-troponin C complex stabilized in this manner is less susceptible to proteolytic attack in the presence of bodily fluids and other components. In this embodiment, a linker of about 6 to about 50 anino acids (and a corresponding number of codons in the cDNA) is preferred, for ease and economics of preparation.

One embodiment of the present invention provides a single-chain troponin I fragment-troponin C polypeptide with a relatively short spacer segment of about 5 to about 50 amino acids. For example, a useful linker polypeptide sequence is $(Gly_4Ser)_3$ which provides a flexible peptide sequence that allows the two subunits to associate. In order to construct the genetic sequence with a linker polynucleotide, an additional 2 codons at each end of the linker polynucleotide are present, which were needed in order to provide unique restriction sites to create the genetic construct of the desired single-chain polypeptide. In one example, codons corresponding to Thr-Ser at the N-terminus of the linker and Ala-Cys at the C-terminus, may be included. Thus, a suitable 19-residue linker may be prepared (genetic sequence SEQ ID NO:5 and peptide SEQ ID NO:6). The above example is only representative of the linked products of the present invention, as other linkers are suitable.

Recombinant methods may be used to prepare the DNA sequence comprising the troponin subunits and the optional linker sequence and to introduce the sequence into a host cell, and standard expression methods are used to express and purify the recombinant polypeptide. These methods are similar to those used for the preparation of fusion proteins such as that described for the two metabolically-coupled yeast enzymes, citrate synthase and malate dehydrogenase (Lindbladh et al., Biochemistry 33:11692–11698 [1994]); in the preparation of single-chain polypeptides comprising the antigen-binding site of antibodies (U.S. Pat. No. 4,946,778); and the preparation of fusion proteins for phage display (U.S. Pat. No. 5,516,637). These methods are known to the skilled artisan.

In the instance in which little or no linker sequence is desired, the troponin I fragment and troponin C cDNA sequences may be joined through suitable techniques known in the art such as the SOEing method using pairs of partially overlapping primers, for example, as described by Hu et al. (1996, Protein Expression and Purification 7:289–293) in which rare codons in human cardiac troponin T were replaced with synonymous major codons. These methods are well known to the skilled artisan.

The recombinant construct is prepared as an expression or cloning vehicle, or plasmid, and introduced into a host cell for expression. Methods for expression of recombinant proteins are known in the art. Once expressed, the single-chain polypeptide may be purified by standard protein purification methods.

Furthermore, the genetic sequences of the troponin I fragment and troponin C may be modified in order to improve the expression of the single-chain polypeptide in a bacterial expression system. These genetic alterations may or may not alter the amino acid sequence of the polypeptide. As is known in the art, certain rare codons present in an expression vehicle reduce expression efficiency, and by changing these codons to synonymous major codons, bacterial expression is improved (for example, as that described for troponin I in co-pending application Ser. No. 08/862,613, filed May 23, 1997, and incorporated herein by reference; and methods of Hu et al., supra, also incorporated herein by reference). In addition, the inclusion of a short nucleotide sequence to the 5' end of the troponin I cDNA (such as that described in Ser. No. 08/862,613) increases bacterial expression, and provides a troponin I polypeptide with an additional six N-terminal amino acids. These optional modifications to increase bacterial expression do not detract from the utility of the single-chain polypeptide for the aforementioned purposes. The short addition to the 5'end of the cDNA to enhance expression may also be added to the N-terminus of a troponin I fragment lacking the native N-terminus, for example, the troponin I fragment described in the Examples herein.

Several troponin I assays are commercially available, all of which operate using different formats, instruments, and assay controls and calibrators. For example the Stratus(R) troponin I assay from Dade utilizes a monoclonal capture and monoclonal detector antibody. The calibrator/control material is an N-terminal peptide from human cardiac troponin I. The operating range of the assay is 0–50 ng/ml, with a sensitivity of 0.6 ng/ml and a cut-off value of 1.5 ng/ml. The Access (R) troponin I assay from Sanofi also utilizes a monoclonal capture and monoclonal detector antibody, but its calibrator/control is a complex of native cardiac troponin I and troponin C. This assay has an operating range of 0–50 ng/ml, a sensitivity of 0.03 ng/ml, and a cut-off value of 0.1 ng/ml. The Opus(R) troponin I assay from Behring utilizes polyclonal antibodies as both capture and detector, has a range of 0–300 ng/ml, a sensitivity of 1 ng/ml and a cut-off value of 2 ng/ml.

Because of the differences in the methodology and components among the above-mentioned assays, commercially-available troponin I calibrators/controls often cannot be used interchangeably among assays. For example, the Stratus(R) calibrators/controls, which use a N-terminal peptide from cardiac troponin I, are not detectable in the Access(R) and Opus(R) assays, as the latter assays' antibodies are not directed to the same N-terminal peptide portion of troponin I used for the controls/calibrators. On the other hand, the Access(R) assay controls, which are detectable in the Access (R) assay with the highest level of sensitivity and cut-off value of all three assays, measure about four times higher in the Opus(R) assay. In contrast, the Opus(R) assay controls are detected poorly by the Stratus(R) assay. These results indicate that it is difficult to interchange assay calibrators/controls between assays, and that the values provided by the controls of one manufacturer's assay can only be used in interpreting assays run on that assay. However, for the constructs of the present invention in which the C-terminal portion of troponin I is absent, assays which detect this portion of the troponin I molecule, for example, the Access assay, would not be suitable for use with the instant compositions.

A single-chain polypeptide of this invention comprising a troponin I fragment and troponin C may also be used for the purification of proteins and other substances including antibodies with an affinity for binding troponin I or troponin C. As noted above, the troponin I portion of the instant compositions is believed to resemble the major circulating form of troponin I after partial degradation by serum proteinases, and perhaps by cardiac intracellular enzymes. For example, the single-chain polypeptide of the present invention may be covalently bound to an insoluble matrix or polymer and situated in a chromatography column. A cell or tissue extract suspected of containing a material that binds troponin, or an antibody preparation raised against troponin, may be passed through the column, whereby it would adhere to the covalently-bound polypeptide. After washing the matrix, the adherent material may be eluted using a concentrated salt solution, a chaotropic agent, or other standard methods used in protein purification. Material binding to the troponin I fragment of the composition would be expected to be more suitable for the detection of the circulating form of troponin I.

A single-chain polypeptide of the present invention may also be useful for the preparation of monoclonal or polyclonal anti-troponin antibodies, using standard methods of animal immunization or hybridoma preparation. For the reasons mentioned above, resulting antibodies are expected to recognize the circulating form of troponin I, and thus improve the sensitivity of an assay made therefrom.

The single-chain polypeptide of the present invention comprising an N-terminal portion of troponin I and troponin C has utility for the preparation of sensitive troponin assays and for the calibration of such assays. By way of example, troponin I may be quantitated by following a particular analytical procedure, for example, by immunoassay, such as those described above. The troponin I level in a sample and the troponin I level in a standard comprising the single-chain polypeptide of the present invention are measured using the particular procedure, wherein the quantity of troponin I in the standard is known. The quantity of troponin I in the sample is then calculated by correlating the measured value of the sample to the measured value of the standard, based on the known quantity of troponin I in this calibrator. As will be seen from the following non-limiting examples, the single-chain polypeptide exhibits superior performance when compared to other troponin calibrators.

EXAMPLE 1

Expression in *E. coli* of a Single-chain Human Cardiac Troponin I Fragment-troponin C Polypeptide with a Linker cDNAs of a human cardiac troponin I fragment corresponding to amino acids 28–110 of the native protein, and troponin C cDNAs were cloned by polymerase chain reaction (PCR) using primers designed from the published cardiac troponin I cDNA sequence (Vallins et al., FEBS Letters 270, 57–61 [1990]) and the troponin C sequence (GenBank AC: X07897). The C-terminus of the troponin I fragment cDNA was linked with the N-terminus of troponin C cDNA through a synthetic linker coding for $(Gly_4Ser)_3$ [genetic and peptide sequences of SEQ ID NO:5 and SEQ ID NO:6, respectively] with an unique restriction site engineered on each end. The single-chain troponin I fragment-C cDNA construct was confirmed by DNA sequencing and cloned into expression vector pET21(Novagen). *E. coli* BL21(DE3) cells, also available from Novagen, were transformed with the resulting plasmid and protein expression was verified by both SDS-PAGE and immunoassays. The single-chain polypeptide described above has a molecular weight of 29,200 Daltons. The genetic and polypeptide sequences are shown in SEQ ID NO: 1 and SEQ ID NO:2, respectively.

The *E. coli* strain expressing the single-chain troponin I fragment-troponin C polypeptide with a linker has been deposited with the American Type Culture Collection (ATCC), 10801 University Boulevard, Manassas Va. 20110–2209, and has been accorded number PTA-396.

EXAMPLE 2

Expression in *E. coli* of a single-chain Human Cardiac Troponin I Fragment-troponin C Polypeptide without a Linker cDNA of a human cardiac troponin I fragment corresponding to amino acids 28–110 of the native protein, and troponin C, were cloned by polymerase chain reaction (PCR) using primers designed from the published cardiac troponin I cDNA sequence (Vallins et al., FEBS Letters 270, 57–61 [1990]) and the troponin C sequence (GenBank AC: X07897). The C-terminus of the troponin I fragment cDNA was linked with the N-terminus of troponin C cDNA through a SphI site which codes for Ala and Cys. The single-chain troponin I fragment-C cDNA construct was confirmed by DNA sequencing and cloned into expression vector pET21 (Novagen). *E. coli* BL21(DE3) cells, also available from Novagen, were transformed with the resulting plasmid and protein expression was verified by both SDS-PAGE and immunoassays. The single-chain polypeptide described above has a molecular weight of 28,100 Daltons. The genetic and polypeptide sequences are shown in SEQ ID NO:3 and SEQ ID NO:4, respectively.

The *E. coli* strain expressing the single-chain troponin I fragment-troponin C polypeptide has been deposited with the ATCC and has been accorded number PTA-395.

EXAMPLE 3

Stability and Utility of the Polypeptide in the Troponin Assay

The immunodetectability of the single-chain troponin I fragment- troponin C polypeptides described in Examples 1 and 2, a complex formed from native cardiac troponin I and troponin C, and native troponin I, were evaluated in the Stratus(R), and Opus(R) assays, following manufacturer's procedures for each assay. The results showed that the immunodetectability on a molar equivalent basis of troponin I was equivalent to or better than that of troponin I in the non-covalent complex and as native, non-complexed troponin I.

EXAMPLE 4

Stability of the Single-chain Troponin I Fragment-troponin C Polypeptide

The stability of the three preparations containing troponin I or fragment used in Example 3 above was followed during incubation in serum at 37° C. for various time periods by determining the molecular weight using a Western blot. Antibodies to the N-terminal portion of troponin I were used. The preparations were (1) recombinant troponin I prepared by standard methods; (2) a non-covalently-bound complex of recombinant troponin I and recombinant C, and (3) the single-chain polypeptide comprising a troponin I fragment and troponin C with an interposed linker peptide, as shown in SEQ ID NO:2. The non-covalently-bound complex of recombinant troponin I and recombinant troponin C was prepared by the procedure of copending and commonly-owned application Ser. No. 08/961,858, filed Oct. 31, 1997, and incorporated herein by reference. Briefly, human cardiac troponin C and a modified troponin I were expressed in *E. coli*. The troponin I was engineered as a recombinant product with six additional N-terminal amino acid residues, to increase its expression; troponin C was expressed with its native amino acid sequence. The modified troponin I in the presence of urea was combined with troponin C, $CaCl_2$ and $MgCl_2$, and shaken gently to promote the formation of troponin I-troponin C complexes.

Results showed that the native troponin I was most susceptible to proteolytic degradation on exposure to serum. The non-covalent troponin I-troponin C complex was more stable, and the single-chain polypeptide of the present invention was most stable.

While the invention has been described and illustrated herein by references to the specific embodiments, various specific material, procedures and examples, it is understood that the invention is not restricted to the particular material combinations of material, and procedures selected for that purpose. Indeed, various modifications of the invention in addition to those described herein will become apparent to those skilled in the art from the foregoing description. Such modifications are intended to fall within the scope of the appended claims.

Various citations to prior publications are mentioned throughout this specification, each of which is incorporated herein by reference in its entirety.

What is claimed is:

1. The single-chain polypeptide set forth as SEQ ID NO.2.

2. A method for quantitating troponin I in a sample comprising the steps of:

i) measuring troponin I in said sample;
   ii) measuring the single-chain polypeptide of claim 1 in a standard, said standard having a known quantity of said polypeptide, which comprises troponin I therein; and
   iii) correlating the troponin I measured in the sample with the known quantity of troponin I measured in the standard, to provide the quantity of troponin I in the sample.

3. The single-chain polypeptide set forth as SEQ ID No.4.

4. A method for quantitating troponin I in a sample comprising the steps of:

i) measuring troponin I in said sample;
   ii) measuring the single-chain polypeptide of claim 3 in a standard, said standard having a known quantity of said polypeptide, which comprises troponin I therein; and
   iii) correlating the troponin I measured in the sample with the known quantity of troponin I measured in the standard, to provide the quantity of troponin I in the sample.

5. A composition comprising the single-chain polypeptide of claim 1 for use as a control or calibrator for a troponin I assay.

6. A composition comprising the single-chain polypeptide of claim 3 for use as a control or calibrator for a troponin I assay.

* * * * *

SEQUENCE LISTING

<160> NUMBER OF SEQ ID NOS: 8

<210> SEQ ID NO 1
<211> LENGTH: 744
<212> TYPE: DNA
<213> ORGANISM: Artificial Sequence
<220> FEATURE:
<223> OTHER INFORMATION: Description of Artificial Sequence: Synthetic
      derived from Homo Sapiens.

<400> SEQUENCE: 1

```
atggcttatg ccacggagcc gcacgccaag aaaaaatcta agatctccgc ctcgagaaaa    60
ttgcagctga agactctgct gctgcagatt gcaaagcaag agctggagcg agaggcggag   120
gagcggcgcg gagagaaggg gcgcgctctg agcacccgct gccagccgct ggagttggcc   180
gggctgggct tcgcggagct gcaggacttg tgccgacagc tccacgcccg tgtggacaag   240
gtggatgaag aggcatgcat ggatgacatc tacaaggctg cggtagagca gctgacagaa   300
gagcagaaaa atgagttcaa ggcagccttc gacatcttcg tgctgggcgc tgaggatggc   360
tgcatcagca ccaaggagct gggcaaggtg atgaggatgc tgggccagaa ccccacccct   420
gaggagctgc aggagatgat cgatgaggtg gacgaggacg gcagcggcac ggtggacttt   480
gatgagttcc tggtcatgat ggttcggtgc atgaaggacg acagcaaagg gaaatctgag   540
gaggagctgt ctgacctctt ccgcatgttt gacaaaaatg ctgatggcta catcgacctg   600
gatgagctga agataatgct gcaggctaca ggcgagacca tcacggagga cgacatcgag   660
gagctcatga aggacggaga caagaacaac gacggccgca tcgactatga tgagttcctg   720
gagttcatga agggtgtgga gtag                                          744
```

<210> SEQ ID NO 2
<211> LENGTH: 247
<212> TYPE: PRT
<213> ORGANISM: Artificial Sequence
<220> FEATURE:
<223> OTHER INFORMATION: Description of Artificial Sequence: Synthetic
      derived from Homo Sapiens.

<400> SEQUENCE: 2

```
Met Ala Tyr Ala Thr Glu Pro His Ala Lys Lys Lys Ser Lys Ile Ser
  1               5                  10                  15

Ala Ser Arg Lys Leu Gln Leu Lys Thr Leu Leu Leu Gln Ile Ala Lys
                 20                  25                  30

Gln Glu Leu Glu Arg Glu Ala Glu Arg Arg Gly Glu Lys Gly Arg
             35                  40                  45

Ala Leu Ser Thr Arg Cys Gln Pro Leu Glu Leu Ala Gly Leu Gly Phe
         50                  55                  60

Ala Glu Leu Gln Asp Leu Cys Arg Gln Leu His Ala Arg Val Asp Lys
 65                  70                  75                  80

Val Asp Glu Glu Ala Cys Met Asp Asp Ile Tyr Lys Ala Ala Val Glu
                 85                  90                  95

Gln Leu Thr Glu Glu Gln Lys Asn Glu Phe Lys Ala Ala Phe Asp Ile
            100                 105                 110

Phe Val Leu Gly Ala Glu Asp Gly Cys Ile Ser Thr Lys Glu Leu Gly
        115                 120                 125

Lys Val Met Arg Met Leu Gly Gln Asn Pro Thr Pro Glu Glu Leu Gln
    130                 135                 140
```

Glu Met Ile Asp Glu Val Asp Glu Asp Gly Ser Gly Thr Val Asp Phe
145                 150                 155                 160

Asp Glu Phe Leu Val Met Met Val Arg Cys Met Lys Asp Asp Ser Lys
                165                 170                 175

Gly Lys Ser Glu Glu Leu Ser Asp Leu Phe Arg Met Phe Asp Lys
            180                 185                 190

Asn Ala Asp Gly Tyr Ile Asp Leu Asp Glu Leu Lys Ile Met Leu Gln
            195                 200                 205

Ala Thr Gly Glu Thr Ile Thr Glu Asp Ile Glu Glu Leu Met Lys
        210                 215                 220

Asp Gly Asp Lys Asn Asn Asp Gly Arg Ile Asp Tyr Asp Glu Phe Leu
225                 230                 235                 240

Glu Phe Met Lys Gly Val Glu
                245

<210> SEQ ID NO 3
<211> LENGTH: 795
<212> TYPE: DNA
<213> ORGANISM: Artificial Sequence
<220> FEATURE:
<223> OTHER INFORMATION: Description of Artificial Sequence: Synthetic
      derived from Homo Sapiens.

<400> SEQUENCE: 3
atggcttatg ccacggagcc gcacgccaag aaaaaatcta agatctccgc ctcgagaaaa      60
ttgcagctga agactctgct gctgcagatt gcaaagcaag agctggagcg agaggcggag     120
gagcggcgcg gagagaaggg gcgcgctctg agcacccgct gccagccgct ggagttggcc     180
gggctgggct tcgcggagct gcaggacttg tgccgacagc tccacgcccg tgtggacaag     240
gtggatgaag agactagtgg tggtggtggt tctggtgggg ggggttctgg tggcggtggt     300
tctgcatgca tggatgacat ctacaaggct gcggtagagc agctgacaga agagcagaaa     360
aatgagttca aggcagcctt cgacatcttc gtgctgggcg ctgaggatgg ctgcatcagc     420
accaaggagc tgggcaaggt gatgaggatg ctgggccaga cccccacccc tgaggagctg     480
caggagatga tcgatgaggt ggacgaggac ggcagcggca cggtggactt tgatgagttc     540
ctggtcatga tggttcggtg catgaaggac gacagcaaag gaaaatctga ggaggagctg     600
tctgacctct tccgcatgtt tgacaaaaat gctgatggct acatcgacct ggatgagctg     660
aagataatgc tgcaggctac aggcgagacc atcacggagg acgacatcga ggagctcatg     720
aaggacggag acaagaacaa cgacggccgc atcgactatg atgagttcct ggagttcatg     780
aagggtgtgg agtag                                                     795

<210> SEQ ID NO 4
<211> LENGTH: 264
<212> TYPE: PRT
<213> ORGANISM: Artificial Sequence
<220> FEATURE:
<223> OTHER INFORMATION: Description of Artificial Sequence: Synthetic
      derived from Homo Sapiens.

<400> SEQUENCE: 4

Met Ala Tyr Ala Thr Glu Pro His Ala Lys Lys Lys Ser Lys Ile Ser
1               5                   10                  15

Ala Ser Arg Lys Leu Gln Leu Lys Thr Leu Leu Leu Gln Ile Ala Lys
            20                  25                  30

Gln Glu Leu Glu Arg Glu Ala Glu Glu Arg Arg Gly Glu Lys Gly Arg
        35                  40                  45

```
Ala Leu Ser Thr Arg Cys Gln Pro Leu Glu Leu Ala Gly Leu Gly Phe
         50                  55                  60

Ala Glu Leu Gln Asp Leu Cys Arg Gln Leu His Ala Arg Val Asp Lys
 65                  70                  75                  80

Val Asp Glu Glu Thr Ser Gly Gly Gly Ser Gly Gly Gly Ser
                 85                  90                  95

Gly Gly Gly Gly Ser Ala Cys Met Asp Asp Ile Tyr Lys Ala Ala Val
             100                 105                 110

Glu Gln Leu Thr Glu Glu Gln Lys Asn Glu Phe Lys Ala Ala Phe Asp
             115                 120                 125

Ile Phe Val Leu Gly Ala Glu Asp Gly Cys Ile Ser Thr Lys Glu Leu
     130                 135                 140

Gly Lys Val Met Arg Met Leu Gly Gln Asn Pro Thr Pro Glu Glu Leu
145                 150                 155                 160

Gln Glu Met Ile Asp Glu Val Asp Glu Asp Gly Ser Gly Thr Val Asp
                 165                 170                 175

Phe Asp Glu Phe Leu Val Met Met Val Arg Cys Met Lys Asp Asp Ser
             180                 185                 190

Lys Gly Lys Ser Glu Glu Glu Leu Ser Asp Leu Phe Arg Met Phe Asp
         195                 200                 205

Lys Asn Ala Asp Gly Tyr Ile Asp Leu Asp Glu Leu Lys Ile Met Leu
     210                 215                 220

Gln Ala Thr Gly Glu Thr Ile Thr Glu Asp Ile Glu Glu Leu Met
225                 230                 235                 240

Lys Asp Gly Asp Lys Asn Asn Asp Gly Arg Ile Asp Tyr Asp Glu Phe
                 245                 250                 255

Leu Glu Phe Met Lys Gly Val Glu
             260

<210> SEQ ID NO 5
<211> LENGTH: 57
<212> TYPE: DNA
<213> ORGANISM: Artificial Sequence
<220> FEATURE:
<223> OTHER INFORMATION: Description of Artificial Sequence: Linkers.

<400> SEQUENCE: 5
actagtggtg gtggtggttc tggtgggggg ggttctggtg gcggtggttc tgcatgc         57

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Linkers.

<400> SEQUENCE: 6

Thr Ser Gly Gly Gly Gly Ser Gly Gly Gly Ser Gly Gly Gly Gly
 1               5                  10                  15

Ser Ala Cys

<210> SEQ ID NO 7
<211> LENGTH: 288
<212> TYPE: PRT
<213> ORGANISM: Homo sapien

<400> SEQUENCE: 7

Met Ser Asp Ile Glu Glu Val Val Glu Glu Tyr Glu Glu Glu Glu Gln
```

```
              1               5                      10                     15
       Glu Glu Ala Ala Val Glu Gln Glu Ala Ala Glu Glu Asp Ala
                       20              25               30
       Glu Ala Glu Ala Glu Thr Glu Thr Arg Ala Glu Glu Asp Glu Glu
                       35              40                   45
       Glu Glu Glu Ala Lys Glu Ala Glu Asp Gly Pro Met Glu Glu Ser Lys
                50              55                  60
       Pro Lys Pro Arg Ser Phe Met Pro Asn Leu Val Pro Pro Lys Ile Pro
        65                  70              75                      80
       Asp Gly Glu Arg Val Asp Phe Asp Asp Ile His Arg Lys Arg Met Glu
                        85              90                  95
       Lys Asp Leu Asn Glu Leu Gln Ala Leu Ile Glu Ala His Phe Glu Asn
                    100             105                 110
       Arg Lys Lys Glu Glu Glu Glu Leu Val Ser Leu Lys Asp Arg Ile Glu
                    115             120                 125
       Arg Arg Arg Ala Glu Arg Ala Glu Gln Gln Arg Ile Arg Asn Glu Arg
                    130             135                 140
       Glu Lys Glu Arg Gln Asn Arg Leu Ala Glu Arg Ala Arg Arg Glu
        145                 150             155                     160
       Glu Glu Glu Asn Arg Arg Lys Ala Glu Asp Glu Ala Arg Lys Lys Lys
                        165             170                 175
       Ala Leu Ser Asn Met Met His Phe Gly Gly Tyr Ile Gln Lys Gln Ala
                    180             185                 190
       Gln Thr Glu Arg Lys Ser Gly Lys Arg Gln Thr Glu Arg Glu Lys Lys
                    195             200                 205
       Lys Lys Ile Leu Ala Glu Arg Arg Lys Val Leu Ala Ile Asp His Leu
           210                 215             220
       Asn Glu Asp Gln Leu Arg Glu Lys Ala Lys Glu Leu Trp Gln Ser Ile
        225                 230             235                     240
       Tyr Asn Leu Glu Ala Glu Lys Phe Asp Leu Gln Glu Lys Phe Lys Gln
                        245             250                 255
       Gln Lys Tyr Glu Ile Asn Val Leu Arg Asn Arg Ile Asn Asp Asn Gln
                    260             265                 270
       Lys Val Ser Lys Thr Arg Gly Lys Ala Lys Val Thr Gly Arg Trp Lys
                    275             280                 285

<210> SEQ ID NO 8
<211> LENGTH: 210
<212> TYPE: PRT
<213> ORGANISM: Homo sapien

<400> SEQUENCE: 8

Met Ala Asp Gly Ser Ser Asp Ala Ala Arg Glu Pro Arg Pro Ala Pro
        1                   5                   10                  15
       Ala Pro Ile Arg Arg Arg Ser Ser Asn Tyr Arg Ala Tyr Ala Thr Glu
                       20              25                  30
       Pro His Ala Lys Lys Lys Ser Lys Ile Ser Ala Ser Arg Lys Leu Gln
                       35              40                  45
       Leu Lys Thr Leu Leu Leu Gln Ile Ala Lys Gln Glu Leu Glu Arg Glu
                    50              55                  60
       Ala Glu Glu Arg Arg Gly Glu Lys Gly Arg Ala Leu Ser Thr Arg Cys
        65                  70              75                      80
       Gln Pro Leu Glu Leu Ala Gly Leu Gly Phe Ala Glu Leu Gln Asp Leu
                        85              90                  95
```

-continued

```
Cys Arg Gln Leu His Ala Arg Val Asp Lys Val Asp Glu Glu Arg Tyr
            100                 105                 110

Asp Ile Glu Ala Lys Val Thr Lys Asn Ile Thr Glu Ile Ala Asp Leu
            115                 120                 125

Thr Gln Lys Ile Phe Asp Leu Arg Gly Lys Phe Lys Arg Pro Thr Leu
            130                 135                 140

Arg Arg Val Arg Ile Ser Ala Asp Ala Met Met Gln Ala Leu Leu Gly
145                 150                 155                 160

Ala Arg Ala Lys Glu Ser Leu Asp Leu Arg Ala His Leu Lys Gln Val
                165                 170                 175

Lys Lys Glu Asp Thr Glu Lys Glu Asn Arg Glu Val Gly Asp Trp Arg
            180                 185                 190

Lys Asn Ile Asp Ala Leu Ser Gly Met Glu Gly Arg Lys Lys Lys Phe
            195                 200                 205

Glu Ser
    210
```